United States Patent [19]

Higashijima

[11] 4,106,478

[45] Aug. 15, 1978

[54] PACKAGED HEAT GENERATOR

[76] Inventor: Sunao Higashijima, No. 17-12, Daita 6-chome, Setagaya-ku, Tokyo, Japan

[21] Appl. No.: 675,569

[22] Filed: Apr. 9, 1976

[30] Foreign Application Priority Data

Jun. 9, 1975 [JP] Japan .............................. 50-78482[U]
Oct. 14, 1975 [JP] Japan .......................... 50-139783[U]
Oct. 14, 1975 [JP] Japan .......................... 50-139784[U]
Oct. 14, 1975 [JP] Japan .......................... 50-148764[U]
Mar. 19, 1976 [JP] Japan ................................. 51-30641

[51] Int. Cl.² .............................................. F24J 1/00
[52] U.S. Cl. .................................... 126/263; 44/3 A; 206/219
[58] Field of Search ........................ 128/403; 126/263; 206/219; 62/4, 530; 128/403; 44/3 R, 3 A

[56] References Cited

U.S. PATENT DOCUMENTS 3,301,250  1/1967  Glasser ................................. 126/263
3,874,504  4/1975  Verakas ................................ 126/263
3,950,158  4/1976  Gossett ................................ 206/219
3,980,070  9/1976  Krupa .................................. 126/263

*Primary Examiner*—Ronald C. Capossela
*Attorney, Agent, or Firm*—Wenderoth, Lind & Ponack

[57] ABSTRACT

A packaged heat generator is used for warming or heating the human body, canned foods and similar objects. It consists of three bags: a first bag contains a composition of metallic powders; a second bag has a vent portion through which air is introduced, and contains the first bag and a composition of oxidation promotors in an isolated relation, such as by two-folding it, before the first use; and a third bag encloses the first and second bags, whereby for use, relatively gentle forces applied to the first and second bags with the third bag completely removed cause the two compositions to be mixed inside the second bag so that the mixtures can provide heat of oxidation and heat of hydration by exposure to air through the second bag.

15 Claims, 11 Drawing Figures

PACKAGED HEAT GENERATOR

BACKGROUND OF THE INVENTION

This invention relates to a packaged heat generator usually known as a body warmer which provides thermal energy by mixing two compositions of metallic powders and oxidation promotors and by exposing the mixtures to air or oxygen in the air.

There is known a prior art by which heat is provided by mixing two or more kinds of elements including metallic powders such as iron powders and oxidation promotors such as humidified activated charcoal powders, and by exposing the mixtures to air. Conventional body warmers or pocket heaters usually in use during the winter days, and other conventional heaters in therapeutic or medical use incorporate the above art. However, those heaters are given little or no consideration of the amount of thermal energy or duration of heating that the heaters should provide, and therefore, they are not satisfactory from its practical standpoint. In other words, the conventional heaters have several problems yet to be solved. First, unless provision is made to prevent the surface oxidation of the metallic powders, the surface oxidation will persist through the period during which they remain not in use or sealed, and at the time the heaters are actually used, they will have lost considerable amounts of heating potential, and last only for a very short period of time. Secondly, if the mixtures are only made to be exposed to air, they will be unable to provide the different temperatures of heating desired depending on the different situation in which they are used. Thirdly, once they are made to begin heating, the heating cannot be interrupted at any desired time, but must continue until it is finally exhausted.

SUMMARY OF THE INVENTION

One object of the present invention is therefore to provide a packaged heat generator which has its capabilities of heating unaffected by preventing the surface oxidation of the metallic powders through the period of time until its first use.

Another object is to provide a packaged heat generator capable of adjustably providing different temperatures of heating depending on the purpose for which it is used.

Still another object is to provide a packaged heat generator which can start heating and stop it at any desired time.

A further object is to provide a packaged heat generator having its heating capabilities unaffected through a long time during which it remains unused.

As it is apparent from the above objects, the heat generator of the invention has a three-package form: the first bag, which is innermost, encloses a composition of powdered metals; the second bag, which is intermediate, has a vent portion and encloses the first bag and a composition of oxidation promoters in an isolated relation, such as by two-folding it, until it is used for the first time; and the thrid bag, which is outermost, is openably fastened and encloses the first and second bags as isolated from each other. For use, the outermost bag is first completely removed, and relatively gentle forces, such as swinging and rubbing, are then exerted on the other two bags, thus causing the two compositions to be mixed together within the second bag so that the mixtures can produce heating by being exposed to air or oxygen in the air in the second bag. The invention has the following merits and features: one is that the heat generation elements are so enclosed in the first bag as to prevent the surface oxidation thereof; a second is that the amount of air can adjustably be supplied through the second bag, which is made possible by means of vent holes of variable dimensions through the second bag: and a third is the controlled function of the second bag, which is made possible by making the second bag exposed to air with the third bag removed, and by cutting the air supply by again enclosing the second bag in the third bag. The above objects have been achieved by the constructional merits and features of the invention described above.

Other objects and advantages of the invention will become apparent from the specification which follows hereinafter with reference to the accompanying drawings which illustrate the construction of the invention for clearer understanding.

DESCRIPTION OF THE PREFERRED EMBODIMENTS

Figure 1:
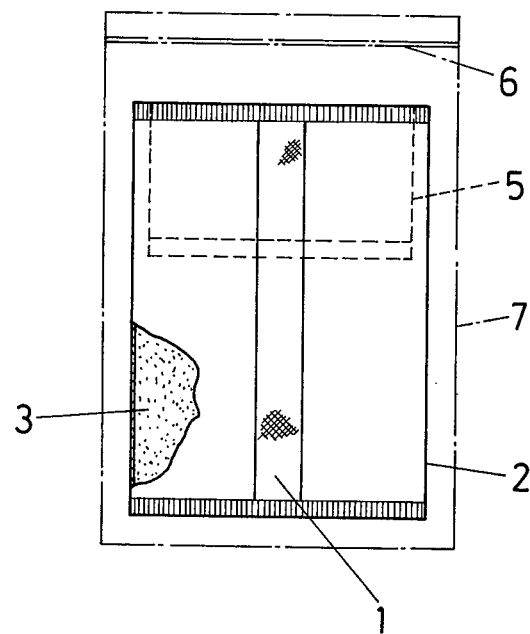
FIG. 1 is a plan view of a first preferred embodiment of the invention.
Figure 2:
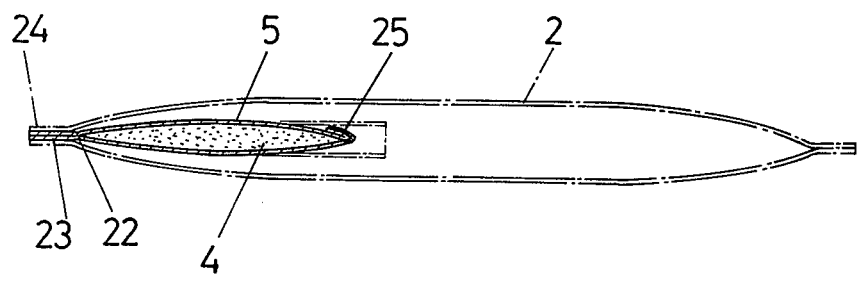
FIG. 2 is a sectional view of the first bag in FIG. 1.

The present invention will be illustrated by way of several preferred embodiments thereof by reference to the accompanying drawings, in which:

A first preferred embodiment of the invention is shown in FIG. 1, in which a second or intermediate enclosure 2, usually having a bag form, has a venting portion 1 on one face thereof through which air is introduced into the bag 2, and contains a composition of oxidation promoters 3 therein. A first or innermost enclosure 5, having a bag form, contains a composition of powdered metals 4 therein. The bag 5 is enclosed inside the second bag 2. The second bag 2, as it encloses the first bag 5 therein, has its opposite ends heat-sealed so that it can keep itself sealed-off from the except through the venting portion 1. Furthermore, the second bag having the first bag 5 contained therein is placed inside a third or outermost enclosure 7 in a bag form which is made of air-impermeable material and has one end 6 thereof openably fastened. In the above embodiment, as shown in details in FIG. 2, the first bag 5 has a generally cylindrical from, and has on one side thereof a portion 23 which is heat-sealed to separate the bag 5 into an end portion 23 and an enclosing portion in which the metallic powders 4 are held. The end of the bag 5 on the other side is open, and has a portion which is folded or bent as shown so as to prevent the content 4 from unexpected escape through the open end. The bag 5 thus constructed is held inside the second bag 2 in such a manner that the end portion 23 of the bag 5 is united with the end portion 24 of the bag 2 by means of heat-sealing so that the bag 5 is secured to the bag 2 at the end portions 23 and 24 of the two bags 5 and 2, and in such a manner that the other end portion of the bag 5 is expandably folded as shown in FIG. 2.

When it is desired to make the heat generator produce heating for use, the outermost bag 7 is first removed, and the remaining bags 2 and 5 then have an application of forces such as swinging and rubbing. Swinging is effected with the heat-sealed portions 23 and 24 held by finger, and rubbing is effected through the second bag 2. During the rubbing operation, the applied forces are transmitted through the second bag 2 to the first bag 5 so that the folded portion can be unfolded as shown by the dot-dash lines in FIG. 2 to allow the contents 4 to come out through the open end of the bag 5 and into the area of the bag 2. The contents 4 then becomes mixed with the oxidation promoters 3 within the bag 2 during a further rubbing operation, and the mixtures also become exposed to air or oxygen in the air through the venting portion 1 of the bag 2 so that the powdered metals become oxidized to provide heat of oxidation and heat of hydration. The heat generator is applied in this state to a part of the human body, for example, that is desired to be warmed or heated. It has other uses of warming or heating articles such as canned foods, for example. In the above embodiment, the metallic powders 4 enclosed in the bag 5 are always isolated from or are not exposed to moisture and air until the heater is actually used, so that the surface oxidation of the metals 4 can be prevented. As mentioned earlier, the third or outermost bag 7 is made of air-impermeable material, and is openably fastened at the portion 6 by means of fastener. Thus, if the bag 2 is desired to stop its heating during the use thereof, it is again placed inside the bag 7, and the portion 6 is closed so that air supply can be cut off the mixtures of the metallic powders 4 and oxidation promoters 3, thus interrupting the heat generation.

Figure 3:
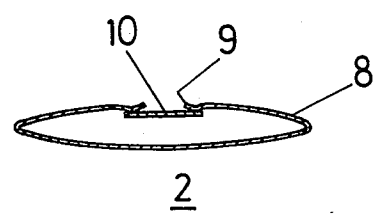
FIG. 3 is a sectional view of the second bag in FIG. 1.
Figure 4:
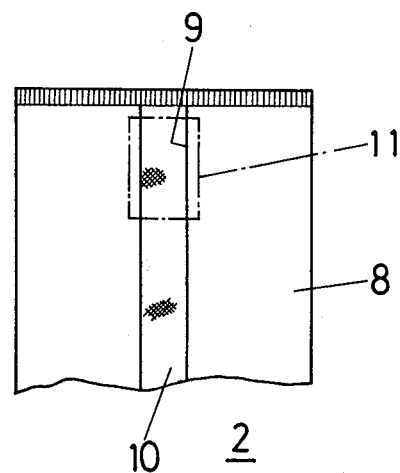
FIG. 4 is a plan view, partially broken away, of the second bag in FIG. 3.
Figure 5:
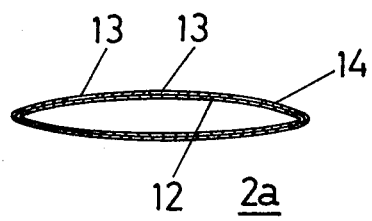
FIG. 5 is a sectional view shwoing the second bag of a second preferred embodiment of the invention.
Figure 6:
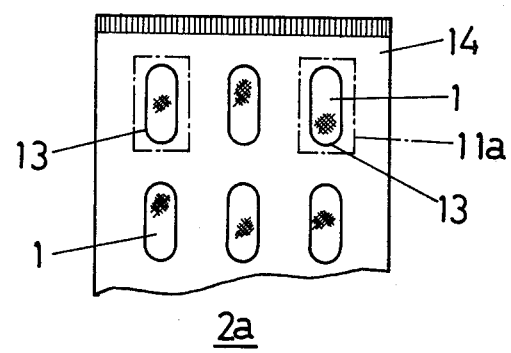
FIG. 6 is a plan view, partially broken away, of the second bag in FIG. 5.

As particularly shown in FIGS. 3 and 4, the bag 2 is made of air-impermeable material such as polyvinyl chloride, for example, having a generally cylindrical form 8 as shown. It has its opposite ends spaced as indicated at 9 through which air is to be introduced into the bag 2. The spacing or channel 9 is covered with a strip of air-permeable material 10 such as unwoven cloth, for example, from the inside of the bag 2, and it serves as the venting portion 1. The channel 9 and the air-permeable material 10 are united by means of heat-sealing the overlapped edges of the two 9 and 10 along the opposite ends of the bag 2. The width of the channel 9 has an influencing effect on the amount of air which can pass therethrough so as to cause the mixtures to produce heat, and the amount or temperature of heating also depends on the amount of air through the channel 9. Therefore, the width or spacing of the channel 9 may previously be determined so that the bag 2 can meet the different needs or purposes, such as locations and/or time of the day or year where it is used. During the use of the heater, its heating can be adjusted to different temperatures desired by applying one or more separate sheets of adhesive sealing material 11 of air-impermeable character to the outside of the venting portion 1 of the bag 2. Application of one or more sheets 11 controls the surface area of the portion 1 through which air can be introduced, and the amount of air through the portion 1 can be regulated accordingly. A plurality of air holes may be provided as a substitute for the above channel 9, as shown in FIGS. 5 and 6. In the second embodiment of FIGS. 5 and 6, a second or intermediate bag 2a has generally the similar form as in the earlier embodiment. The bag 2a consists of two kinds of materials which have a generally like form, and are laminated as shown in FIG. 5. One material 12 has an air-permeable character, and other material 14 has an air-impermeable character and has a plurality of vent holes 13, 13 at regularly spaced intervals as shown in FIG. 6. The vent holes 13, 13 serve as the venting portion 1 through which air is introduced into the bag 2a. The number of the vent holes 13, 13 effectively influences the amount of air therethrough, and accordingly the temperature of heating. Thus, any number of air holes 13, 13 may previously be chosen depending on the purpose for which the heater is used. Otherwise, one or more sheets 11a of the same character as in the first embodiment may be applied to the corresponding holes so that the temperature of heating can be regulated as desired.

Figure 7:
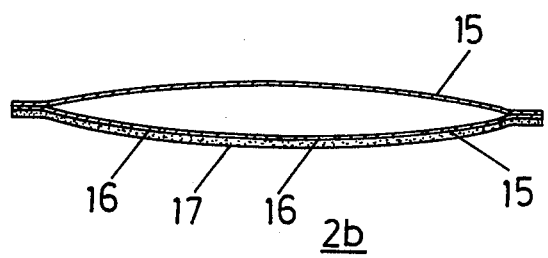
FIG. 7 is a sectional view showing the second bag of a third preferred embodiment of the invention.
Figure 8:
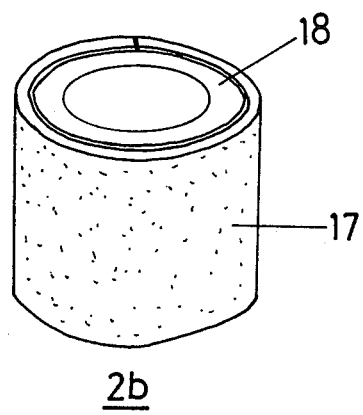
FIG. 8 is a perspective view showing the second bag of FIG. 7 as it is used with a canned food, for example.

In a third embodiment of FIG. 7, an intermediate bag 2b consists of air-impermeable base material 15 of a generally cylindrical form having on one side a plurality of vent holes 16, 16 at regularly spaced intervals, and a coating of air-permeable and heat-insulating material 17 applied over said one side of the material 15. As easily understood from the above, the thermal energy or heating produced inside the bag 2b will not escape through the heat-insulating coating 17 on the one side, but will totally and effectively be delivered through the vent holes 16, 16 of the air-impermeable material 15 on the other side. As shown in FIG. 8, for example, a canned food 18 is wrapped by the bag 2b for the purpose of heating the food or keeping it warm. As seen from FIG. 8, wrapping is made so that the can body can be surrounded with the bag 2b with the side of the heat-insulating material 17 outward. In this case, it is also possible to have different temperatures of heating by adjusting the holes 16, 16 to different diameters or providing the holes 16, 16 at different locations. In a varied form of the embodiment of FIG. 8, the bag 2b may consist of, on one side, a sheet of air-impermeable material 15 having vent holes 16, 16, and on the other side a sheet of air-permeable and heat-insulating material 17, the two sheets 15 and 17 being united by heat-sealing the ends thereof to form a bag.

Figure 9:
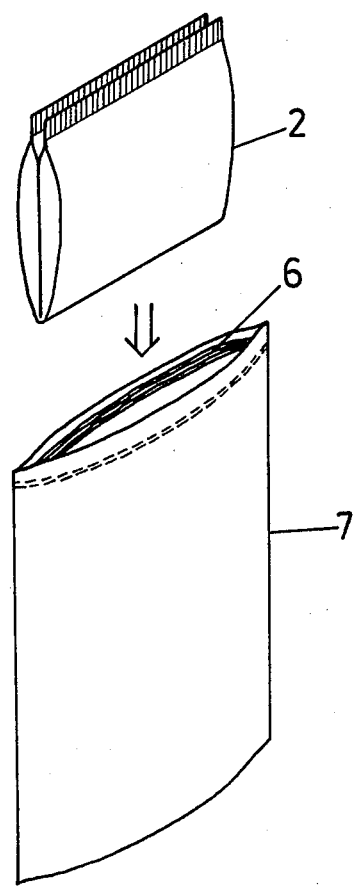
FIG. 9 is a perspective view showing the second bag of a fourth preferred embodiment of the invention.
Figure 10:
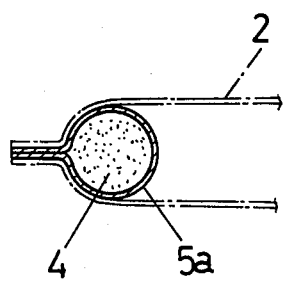
FIG. 10 is a sectional view showing the first bag of a fifth preferred embodiment of the invention.

A varied form of the embodiment of FIG. 1 is shown in FIG. 9, has the following consideration: if there should be unexpectedly some slight leaks of the content 4 out of the bag 5 under occasional swinging or shaking forces during the packaging work of assorted products for shipping or during the transportation thereof, and then if the leaks should become mixed with the oxidation promotors 3 within the bag 2, the mixtures would be likely to produce some amounts of heating by being exposed to an amount of air which is assumed to remain in the bag 7. According to the embodiment shown in FIG. 9, the bag 2 in FIG. 1 is two-foldable at mid-position so that the bag 5 can definitely be isolated from the content 3, and is enclosed as folded within the bag 7. In this manner, if the products in a shipping carton should have occasional swinging or other external forces during the transportation, there will be no unexpected leaks of the content 4 with no accompanying mixture of the two different compositions. This means that the heat generation will never take place under the above circumstances. It should also be noted that there is no other particular means of keeping the two compositions away from each other than by simply two-folding or bending in two parts. The bag 5 may have a further varied form as shown in FIG. 10, which can reliably prevent the surface oxidation of the chemicals 4 therein. As particularly shown in FIG. 10, an innermost bag 5a is made of material which has such a character as to break by application of relatively gentle or moderate forces such as pressure, bending or impact, and it contains a composition of powdered metals therein. The bag 5a is enclosed in the intermediate bag 2, and has an end thereof united by means of heat-sealing with the corresponding end of the bag 2. According to the varied form in FIG. 10, for use, relatively gentle forces are applied by way of the bag 2 to the bag 5a, causing the bag 5a to collapse so that the compositions 4 and 3 can be mixed together, and heating can take place as the composition 4 become oxidized by being exposed to air through the bag 2. In this embodiment, the work of placing the bag 5a inside the bag 2 can be carried out with greater ease than the work in the earlier embodiments. A further advantage of the embodiment of FIG. 10 is that as the composition 4 remain tightly sealed by the bag 5a until the bag is made to collapse, they cannot be exposed to air during that period, with no accompanying surface oxidation. Those advantages of the bag 5a shown in FIG. 10 have a good effect on keeping its capability of heating unaffected during a long period of time until it is made to collapse for use.

Figure 11:
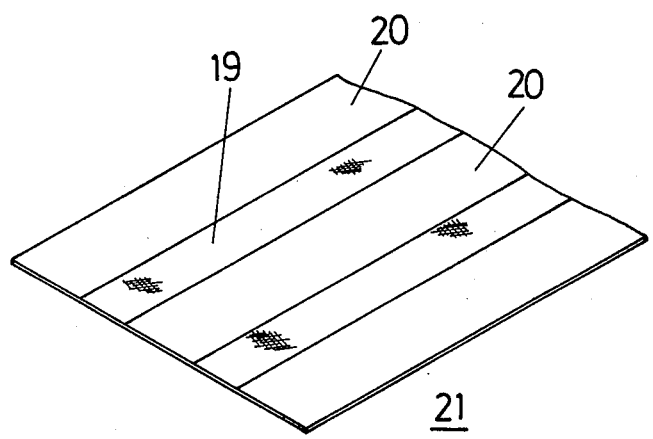
FIG. 11 is a perspective view showing the second bag of different materials of a sixth preferred embodiment of the invention.

In an example shown in FIG. 11, an intermediate bag 21 is made of air-permeable material 19, such as paper, unwoven cloth or cloth, and has a printing or coating 20 of synthetic resin ink over the material 19, or a coverage of synthetic resin material fused and united by heating to the material 19, the coating or coverage 20 serving to close the vent holes of the air-permeable material 19. In this example, the coating of ink may have the advertising effect if it is made to represent appropriate letters, figures or patterns.

Table 1 shows the two compositions of the metallic powders and the oxidation promotors, which are used for the various forms of the invention described heretofore.

Table 1

| 1. Composition of Metallic Powders | |
|---|---|
| Elements | Contents percent(%) by weight |
| Iron powders | 65 to 80 |
| Aluminum powders | 5 to 8 |
| Ferro-silicon powders | 5 to 8 |
| Silicon powders | 3 to 6 |
| Graphite | 8 to 11 |
| Bentonite | 0 to 5 |

| 2. Composition of Oxidation Promotors | |
|---|---|
| Elements | Contents percent(%) by weight |
| Humidified activated charcoal powders | 52 to 55 |
| Fabric powders | 10 to 12 |
| Chaffed charcoal powders | 7 to 9 |
| Zeolite | 7 to 9 |
| Bentonite | 0 to 9 |
| Other oxidation promotors | 9 to 12 |

As seen from the above table, the principal elements of the two compositions are iron powders and humidified activated charcoal powders, respectively. In the composition of the metal powders, on one hand, aluminum powders and ferro-silicon powders can promote the heat generation of the iron powders. Silicon powders and graphites prevent the surface oxidation of the iron powders. Because of its good base changeability, bentonite has a good effect on preventing the surface oxidation of the iron powders particularly through the period of time during which they are not used. In the oxidation promotors, on the other hand, chaffed charcoal powders and zeolite have the effect of absorbing and holding the moisture which evaporates from the activated charcoal powders which become humidified during the heat generation of the metallic powders. This has a favorable effect on lengthening the life of the heat generating capabilities. Because of its swelling character, bentonite promotes the moisture holding function of the powdered fabrics, etc., and also has the effect of gradually humidifying the activated charcoal powders. Other elements which promote the oxidation of the metallic powders include sodium chloride known as common salt, ferric chloride and copper chloride, for example, which are dissolved in the moisture which makes the activated charcoal powders humidified.

About 5 to about 50% in total of the two compositions in the bag 2 or 2a with respect to the capacity of the bag 2 or 2a is preferably chosen so that an appropriate amount of room can be provided for accommodating those two compositions inside the bag 2 or 2a, the reason for which will be clarified later. This room provides a space in which the moisture from the oxidation promotors can be held, thus enhansing the water-holding function of the powdered fabrics, etc. referred to earlier, and preventing the oxidation promoters from becoming dry. The relationship between the total amount of the two compositions of the heat-generating elements and the capacity of the bag 2 or 2a is now considered: if the former is less than 5% with respect to the latter, the elements will produce only a small amount of heat, as compared with considerable amounts of the thermal loss from the surface of the bag 2 or 2a, and insufficiently low temperatures of heating will accompany; and if the amount of the elements is more than 50%, the movement of the elements within the bag 2 or 2a will be restricted when the bag 2 or 2a has the swinging or shaking forces, and the resulting mixtures will become uniform which makes the heating limited to very low temperatures. As easily understood from the above observations, therefore, the range of between 5% and 50% of the elements is preferable. As an element of the oxidation promotors, chaffed charcoal powders have their cupped forms having rugged surfaces, and therefore have a good effect on holding the moisture from the activated charcoal powders.

If proper amounts of smelling or deodorizing substances or volatile elements such as disinfectors, insecticides or insect powders are added to the metallic powders, the heat generator can provide an emission of fragrant smells, or add to the functions of deodorizing, disinfecting, etc., the neighboring area of the location where it is applied.

The packaged heat generator described heretofore consists essentially of three bags, the innermost bag containing a composition of powdered metals, the intermediate bag containing the innermost bag and a composition of oxidation promotors in an isolated relation before the first use, and the outermost bag containing the two earlier-mentioned bags. The heat generator provides the following advantages. As the metallic powders are enclosed in the innermost bag constructed to prevent the surface oxidation of the metallic powders therein, they can remain unaffected during a very long period of time, and for all that, they can still provide the different temperatures of heating as desired. Because of its own construction or by means of using one or more separate sheets of adhesion sealing material, the intermediate bag can be made to provide different temperatures of heating which depend on the purpose for which it is used. Furthermore, the outermost bag, openably fastened, provides chances of using the heater as many times as possible, as the heating can be discontinued and resumed at any desired time by again enclosing the intermediate bag in the outermost bag.

Although the invention has been described by way of the several embodiments thereof, it should be understood that various changes and modifications may be made without departing from the spirit and scope of the invention.

What is claimed is:

1. A packaged heat generator for warming objects, said heat generator comprising:
   heat generating material;
   first enclosing means of air-impermeable material surrounding said heat generating material for containing said heat generating material therein;
   second enclosing means of air impermeable material surrounding said first enclosing means for containing said first enclosing means therein, said second enclosing means having air passage means therethrough for allowing air to enter into said second enclosing means;
   oxidation promotion material within said second enclosing means and outside of said first enclosing means;
   third enclosing means of air impermeable material surrounding said second enclosing means for removably containing said second enclosing means therein, said third enclosing means being openable and recloseable at one end.

2. A heat generator as claimed in claim 1, wherein said second enclosing means is folded into two portions along a fold line inside said third enclosing means, said first enclosing means being on one side of said fold line and said oxidation promotion material being on the other side of said fold line, whereby said heat generating material is securely kept away from said oxidation promotion material.

3. A heat generator as claimed in claim 1, wherein said air passage means is comprised of:
   a channel extending longitudinally along one side of said second enclosing means; and
   a strip of air-permeable material beneath and lining said channel.

4. A heat generator as claimed in claim 1, wherein said second enclosing means is comprised of two laminated sheet materials, one being air-permeable, and the other being air-impermeable with a plurality of air holes therethrough.

5. A heat generator as claimed in claim 1, wherein said second enclosing means is comprised of:
   a generally cylindrical air-impermeable base material having on one side thereof a plurality of air holes; and
   a coating of air-permeable and heat-insulating material applied over said side of said air-permeable base material having said holes therein.

6. A heat generator as claimed in claim 1, wherein said heat generating material is a mixture of powdered metals selected from the group consisting of:
   powdered iron;
   powdered aluminum;
   powdered ferro-silicon;
   powdered silicon; and
   graphite.

7. A heat generator as claimed in claim 1, wherein said heat generating material is a mixture of powdered metals selected from the group consisting of:
   powdered iron;
   powdered aluminum;
   powdered ferro-silicon;
   powdered silicon;
   graphite; and
   bentonite.

8. A heat generator as claimed in claim 1, wherein said oxidation promoting material is a mixture of materials selected from the group consisting of:
   humidified activated charcoal powders;
   powdered fabrics;
   chaffed charcoal powders; and
   zeolit.

9. A heat generator as claimed in claim 1, wherein said oxidation promoting material is comprised of a mixture of materials selected from the group consisting of:
   humidified activated charcoal powders;
   powdered fabrics;
   chaffed charcoal powders;
   zeolite; and
   bentonite.

10. A heat generator as claimed in claim 1, wherein said first enclosing means is open at one end thereof and is expandably folded closed, and the other end thereof is heat sealed to said second enclosing means.

11. A heat generator as claimed in claim 1, wherein said first enclosing means is adapted to collapse by application of pressure, bending or gentle impact.

12. A heat generator as claimed in claim 1, wherein the amounts of said heat generating material and said oxidation promoting material require substantially 5% to 50% of the capacity of said second enclosing means.

13. A heat generator as claimed in claim 1, further comprising, in said first enclosing means, materials selected from the group consisting of:
   fragrant smelling substances;
   deodorant substances;
   insecticides; and
   insect repellent substances.

14. A heat generator as claimed in claim 1, wherein said second enclosing means is comprised of:
   air-permeable material of a generally cylindrical form; and synthetic resin material attached by means of a heat-fusion to at least a portion of said air-permeable material whereby portions of said air-permeable material are impermeable to air.

15. A packaged heat generator for warming objects, said heat generator comprising:
   heat generating material;
   first enclosing means of air-impermeable material surrounding said heat generator material for containing said heat generating material therein;

second enclosing means of air impermeable material surrounding said first enclosing means for containing said first enclosing means therein, said second enclosing means having air passage means therethrough for allowing air to enter into said second enclosing means, said air passage means being comprised of:

a channel extending longitudinally along one side of said second enclosing means, and a strip of air-permeable material beneath and lining said channel;

oxidation promotion material within said second enclosing means and outside of said first enclosing means whereby said oxidation material is separated from said heat generating material; and third enclosing means of air impermeable material surrounding said second enclosing means for removably containing said second enclosing means therein, said third enclosing means being openable and recloseable at one end.

* * * * *